United States Patent
Papaloïzos (10) Patent No.: US 10,786,357 B2
(45) Date of Patent: Sep. 29, 2020

(54) ARTHRODESIS IMPLANT AND SURGICAL KIT COMPRISING SUCH AN IMPLANT

(71) Applicant: IN2BONES, Ecully (FR)

(72) Inventor: Michaël Papaloïzos, Geneva (CH)

(73) Assignee: IN2BONES, Ecully (FR)

( * ) Notice: Subject to any disclaimer, the term of this patent is extended or adjusted under 35 U.S.C. 154(b) by 114 days.

(21) Appl. No.: 15/961,244

(22) Filed: Apr. 24, 2018

(65) Prior Publication Data

US 2018/0303615 A1    Oct. 25, 2018

(30) Foreign Application Priority Data

Apr. 25, 2017   (FR) .................................... 17 53605

(51) Int. Cl.
*A61F 2/42* (2006.01)
*A61B 17/72* (2006.01)
(Continued)

(52) U.S. Cl.
CPC ...... *A61F 2/30771* (2013.01); *A61B 17/7291* (2013.01); *A61F 2/4225* (2013.01);
(Continued)

(58) Field of Classification Search
CPC .......... A61F 2002/30622; A61F 2/4225; A61F 2002/4228; A61F 2002/4233;
(Continued)

(56) References Cited

U.S. PATENT DOCUMENTS

| 5,417,692 A | * | 5/1995 | Goble | .................... A61B 17/68 |
| | | | | 433/173 |
| 2010/0036439 A1 | * | 2/2010 | Lavi | ................... A61B 17/7291 |
| | | | | 606/308 |

(Continued)

OTHER PUBLICATIONS

Preliminary Search Report dated Jan. 8, 2012 in connection with French Patent Application No. FR-17 53605.

*Primary Examiner* — David H Willse
*Assistant Examiner* — Javier G Blanco
(74) *Attorney, Agent, or Firm* — John P. White; Gary J. Gershik; Cooper & Dunham LLP (57) ABSTRACT

An arthrodesis implant (1) for promoting the osseous fusion of a first bone (2) with a second bone (3), the implant (1) comprising a primary component (4) including a primary anchoring body (5) and a male connector (6), and a secondary component (7) including a secondary anchoring body (8) and a female connector (9), the female connector (9) comprising: a main body (10) which extends longitudinally between a rear end (11) linked to the secondary anchoring body (8) and an opposite front face (12), and which has a lateral wall (14) linking the rear end (11) to the front face (12), a housing (15) formed within the main body (10) and configured to receive the male connector (6) in order to link together the primary (4) and secondary (7) components, the female connector (9) further comprising an opening (18) which is formed in the main body (10), in communication with the housing (15), and which extends continuously on both the front face (12) and the lateral wall (14), and which (Continued)

is sized and configured to enable a lateral introduction of the male connector (6) into the housing (15) via the opening (18), each of the primary (4) and secondary (6) components forming an integral part made in one piece, and the primary (5) and secondary (8) anchoring bodies being respectively designed to ensure the insertion and anchoring of the primary component (4) into the first bone (2), and of the secondary component (7) into the second bone (3), by impaction or by forced wedging.

5 Claims, 6 Drawing Sheets

(51) Int. Cl.
     *A61F 2/30*       (2006.01)
     *A61F 2/46*       (2006.01)
(52) U.S. Cl.
     CPC .......... *A61F 2/4241* (2013.01); *A61F 2/4606* (2013.01); *A61B 17/7266* (2013.01); *A61F 2002/3085* (2013.01); *A61F 2002/30235* (2013.01); *A61F 2002/30367* (2013.01); *A61F 2002/30448* (2013.01); *A61F 2002/30622* (2013.01); *A61F 2002/4228* (2013.01); *A61F 2002/4243* (2013.01)

(58) Field of Classification Search
     CPC ............ A61F 2/4241; A61F 2002/4243; A61F 2002/4251; A61B 17/7291
     See application file for complete search history.

(56) References Cited

U.S. PATENT DOCUMENTS

| | | | |
|---|---|---|---|
| 2010/0256639 A1 | 10/2010 | Tyber et al. | |
| 2011/0004255 A1* | 1/2011 | Weiner | A61B 17/7291 606/301 |
| 2011/0118739 A1* | 5/2011 | Tyber | A61B 17/8685 606/62 |
| 2013/0030475 A1 | 1/2013 | Weiner et al. | |
| 2013/0274814 A1* | 10/2013 | Weiner | A61B 17/8875 606/301 |
| 2014/0018930 A1 | 1/2014 | Oster | |
| 2017/0065424 A1 | 3/2017 | Lauf et al. | |

* cited by examiner

ARTHRODESIS IMPLANT AND SURGICAL KIT COMPRISING SUCH AN IMPLANT

CROSS-REFERENCE TO RELATED APPLICATION

This application claims priority of French Patent Application No. FR-17 53605, filed Apr. 25, 2017, the entire contents of which are hereby incorporated by reference into the application.

The invention relates to the general field of osteosynthesis surgical implants, and in particular to phalangeal implants intended to be placed in the body of a patient, at the level of his hand or foot, in order to enable the fusion of two phalanges. The invention also relates to the fields of surgical kits comprising such implants.

More specifically, the invention concerns an arthrodesis implant for promoting the osseous fusion of a first bone with a second bone, said implant comprising a primary component including a primary anchoring body and a male connector, and a secondary component including a secondary anchoring body and a female connector, said female connector comprising:
- a main body which extends longitudinally between a rear end linked to said secondary anchoring body and an opposite front face, and which has a lateral wall linking said rear end to said front face;
- a housing formed within said main body and configured to receive said male connector in order to link together said primary and secondary components.

The invention also concerns a surgical kit comprising an arthrodesis implant for promoting the osseous fusion of a first bone with a second bone.

In order to treat some osseous pathologies, in particular of the phalanges, such as interphalangeal deformations, claw or hammer toes, or still osteoarthritis, an arthrodesis should be sometimes performed, that is to say an interosseous fusion should be sometimes caused so as to secure one bone relative to the other. In the case of phalanges for example, it is known to place an intramedullary implant during a surgical intervention, which aims at securing two phalanges relative to each other, in order to cause their osseous fusion. Such known arthrodesis implants are most often made so as to form a part made in one piece, which allows improving their longevity in the body of the patient, for example so as not to have to be removed from said body. Alternatively, there are also known arthrodesis implants including, on the contrary, two distinct complementary components, namely a primary component intended to be anchored in the medullary canal of one of the two phalanges, and a secondary component which may be anchored in the medullary canal of the second phalanx. These primary and secondary components include complementary connectors designed to link and lock together said primary and secondary components.

While such known implants are generally satisfactory, they still have some drawbacks and seem to be perfectible. In particular, the setting of these known implants may sometimes prove to be difficult to the surgeon and traumatic to the patient. Indeed, placing them in the body of the patient requires the surgeon to proceed beforehand to a relatively considerable articular distraction (that is to say spacing) of the phalanges, in order to be able to ensure the mating of the male and female connectors and the coupling of the primary and secondary components. However, such a distraction of the phalanges may prove to be harmful to the tendons and surrounding soft tissues, possibly leading to severe pain for the patient and to the lengthening of the period of remission of the latter.

The objects assigned to the present invention aim consequently at overcoming the different drawbacks enumerated in the foregoing and at providing a new arthrodesis implant whose placing is at the same time rapid, easy and particularly barely traumatic to the patient, in particular for the tendons and soft tissues surrounding the joint to be treated.

Another object of the invention aims at providing a new implant, particularly robust and resistant, and whose holding in the body of the patient is particularly reliable.

Another object of the invention aims at providing a versatile new implant adaptable to the morphology of each patient while enabling a relatively rapid and painless arthrodesis.

Another object of the invention aims at providing a new implant whose manufacture is relatively easy and inexpensive.

Another object of the invention aims at providing a new implant allowing to reduce the cost of the surgical intervention for setting the implant, while reducing the risk for the health of the patient related to the setting of the implant and to the therapy.

Another object of the invention aims at providing a new implant allowing to treat an osseous pathology of the patient in a particularly effective and rapid manner.

Another object of the invention aims at providing a new surgical kit comprising such an improved implant as well as surgical instruments enabling an easy, rapid and accurate setting of the latter in the body of a patient.

The objects assigned to the invention are achieved by means of an arthrodesis implant for promoting the osseous fusion of a first bone with a second bone, said implant comprising a primary component including a primary anchoring body and a male connector, and a secondary component including a secondary anchoring body and a female connector, said female connector comprising:
- a main body which extends longitudinally between a rear end linked to said secondary anchoring body and an opposite front face, and which has a lateral wall linking said rear end to said front face,
- a housing formed within said main body and configured to receive said male connector in order to link together said primary and secondary components, said female connector further comprising an opening which is formed in said main body, in communication with said housing, and which extends continuously on both said front face and said lateral wall, and which is sized and configured to enable a lateral introduction of the male connector into said housing via said opening, each of said primary and secondary components forming an integral part made in one piece, and said primary and secondary anchoring bodies being respectively designed to ensure an insertion and an anchoring of the primary component into the first bone, and of the secondary component into the second bone, by impaction or by forced wedging.

The objects of the invention are also achieved by means of a surgical kit comprising an arthrodesis implant for promoting the osseous fusion of a first bone with a second bone, said arthrodesis implant being in accordance with the foregoing, and said kit also comprising:
- a first gripping instrument provided with a first endpiece for securing the primary component of the implant with the first gripping instrument, via the male connector of the primary component;

a second gripping instrument provided with a second endpiece for securing the secondary component of the implant with the second gripping instrument, via the female connector of the secondary component.

Other particularities and advantages of the invention will appear and emerge in more detail upon reading the description made hereinafter, with reference to the appended drawings, given only as an illustrative and non-limiting examples, in which.

The invention concerns as such an arthrodesis implant 1 (FIG. 1), that is to say a surgical implant 1 intended to be placed in the body of a patient, whether human or animal, at the level of his bones, for example during a surgical operation performed under local or general anesthesia. The implant 1 of the invention allows performing an arthrodesis of a first bone 2 with a second bone 3, that is to say it allows promoting the osseous fusion of these first 2 and second 3 bones. The osseous fusion is preferably performed at the level of a joint connecting the first bone 2 to the second bone 3, so as to eliminate said osseous fusion. Alternatively, the implant of the invention may be implemented to promote the osseous fusion between two distinct osseous bodies originating from the same bone (or from different bones) of the patient. In particular, such a surgical operation may allow, in the case where the patient suffers for example from an interarticular osteoarthritis, eliminating the pain experienced by the patient by merging the affected joint. Alternatively, the surgery may allow treating for example an interphalangeal deformation, or claw or hammer toes. Thus, the implant 1 of the invention may be advantageously inserted at the level of the joint between two bones of the vertebral column, of the knee, or of the elbow. Yet preferably, the implant 1 of the invention forms a phalangeal intramedullary implant, that is to say an implant intended to be implemented at the level of phalanges of a hand or of a foot of a patient. Thus, the first bone 2 forms a first phalanx and the second bone 3 forms a second phalanx of the same finger or toe as the first phalanx (FIGS. 7 to 9 and 15 to 17). Still more specifically, the implant 1 is preferably intended to be positioned at the level of a distal interphalangeal joint of a hand of a patient, that is to say at the level of the joint separating the distal and intermediate phalanges, preferably of the forefinger, of the middle finger, or of the ring finger.

Figure 1:
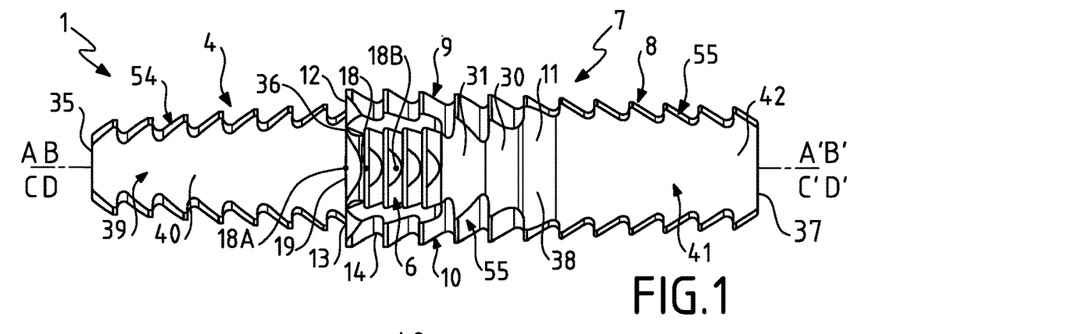
FIG. 1 illustrates, according to a top view, a preferred first embodiment of the implant of the invention.
Figure 9:
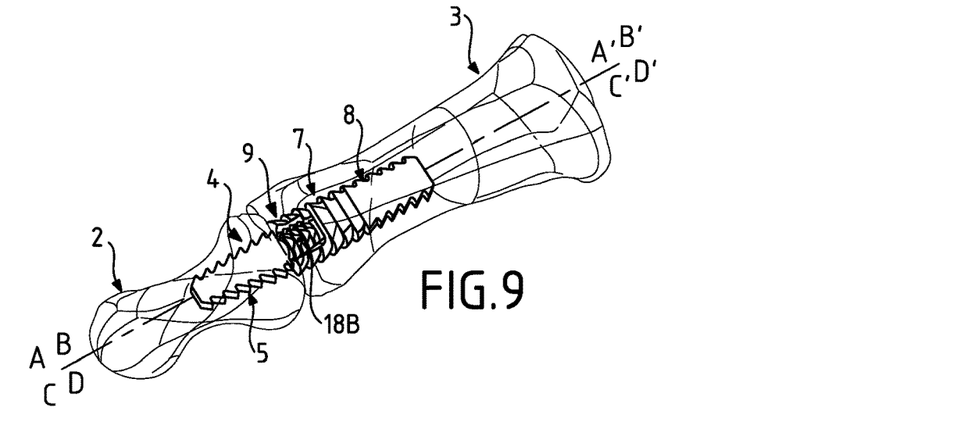
Figures 10, 11:
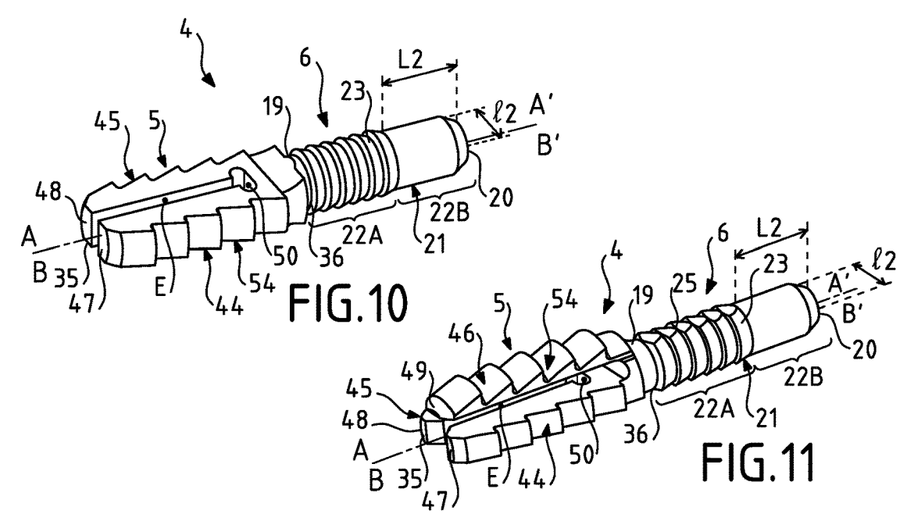
FIGS. 10 to 13 illustrate, according to perspective views, variants of the primary component of the implant of the invention, according to a preferred second embodiment of the latter.
Figures 12, 13:
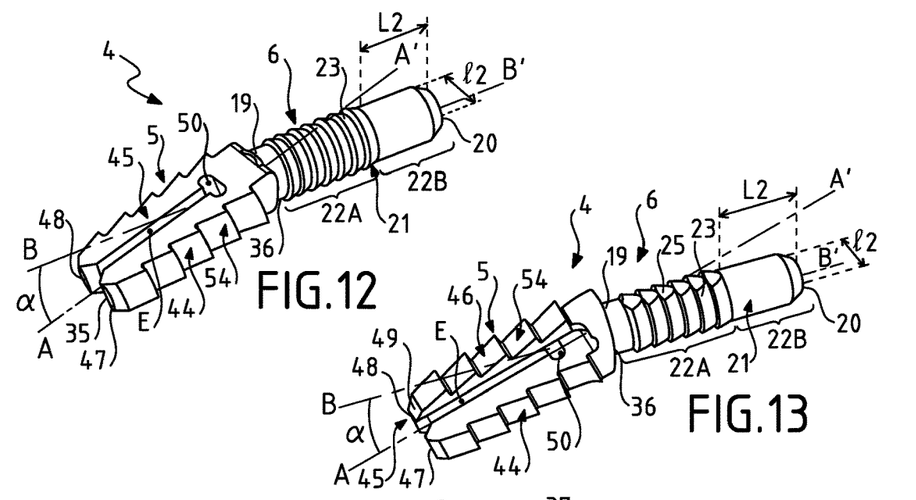
Figure 17:
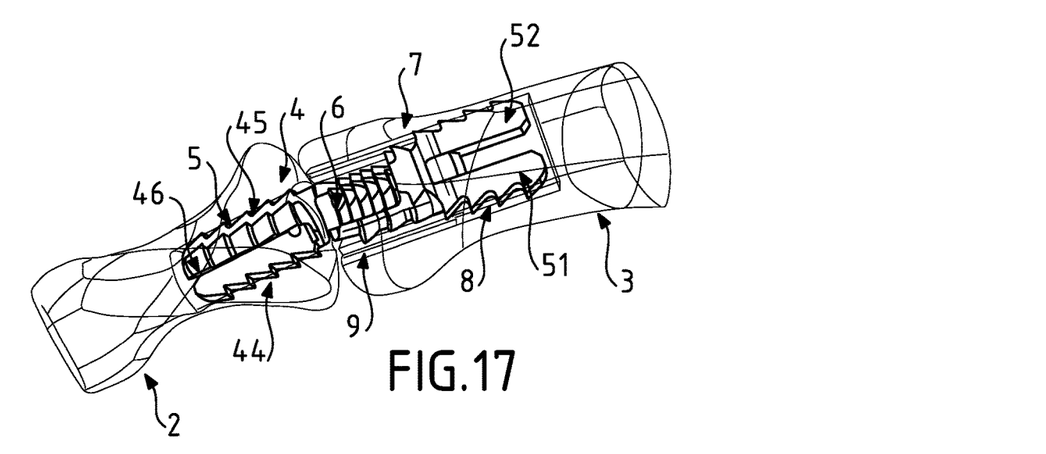
Figure 18:
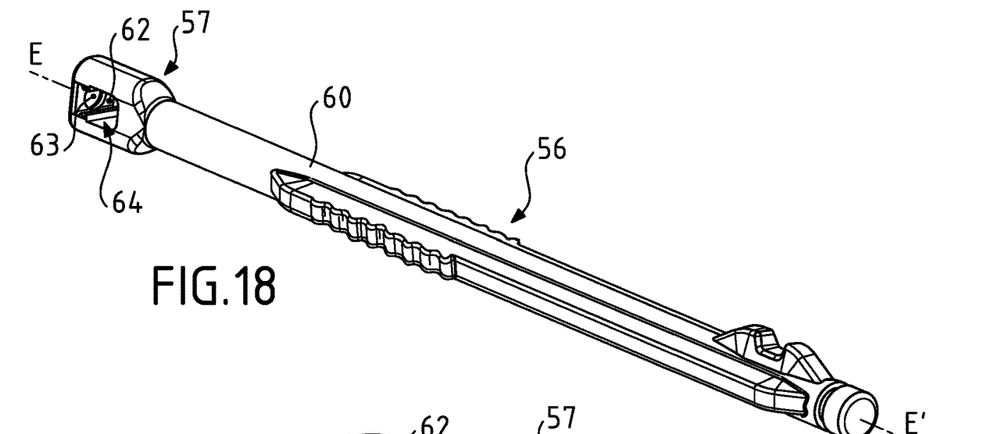
FIG. 18 illustrates, according to a perspective view, the first gripping instrument of the kit of the invention, provided with a first endpiece for securing the primary component of an implant in accordance with the invention.
Figure 19:
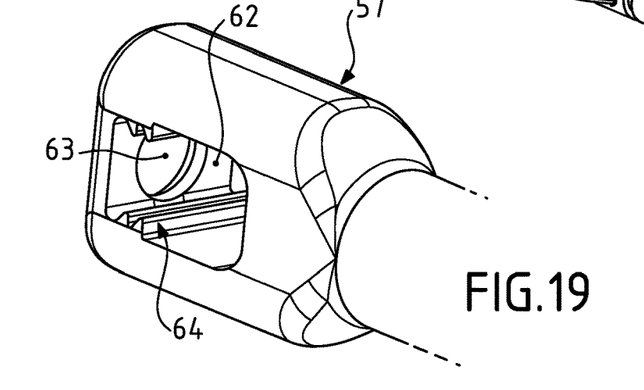
FIG. 19 illustrates, according to a perspective view, the first endpiece of this first instrument.
Figure 20:
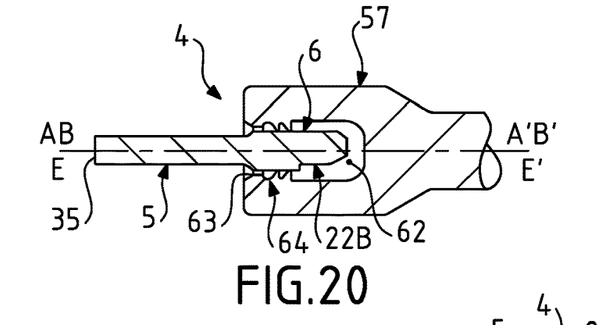
FIGS. 20 and 21 illustrate, according to longitudinal sectional views, unlocked (FIG. 20) and locked (FIG. 21) configurations of the primary component of an implant in accordance with the invention in the endpiece of FIG. 19.
Figure 21:
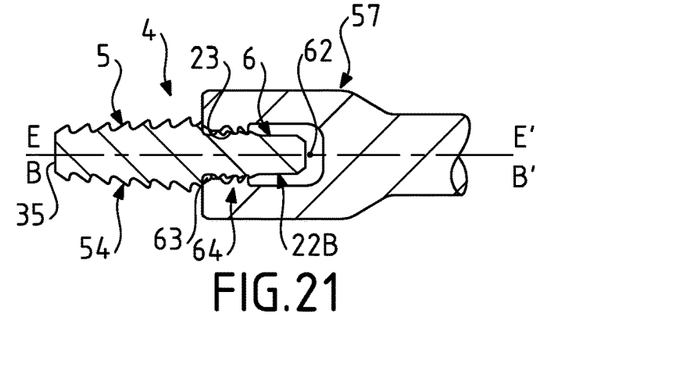
Figures 22, 23:
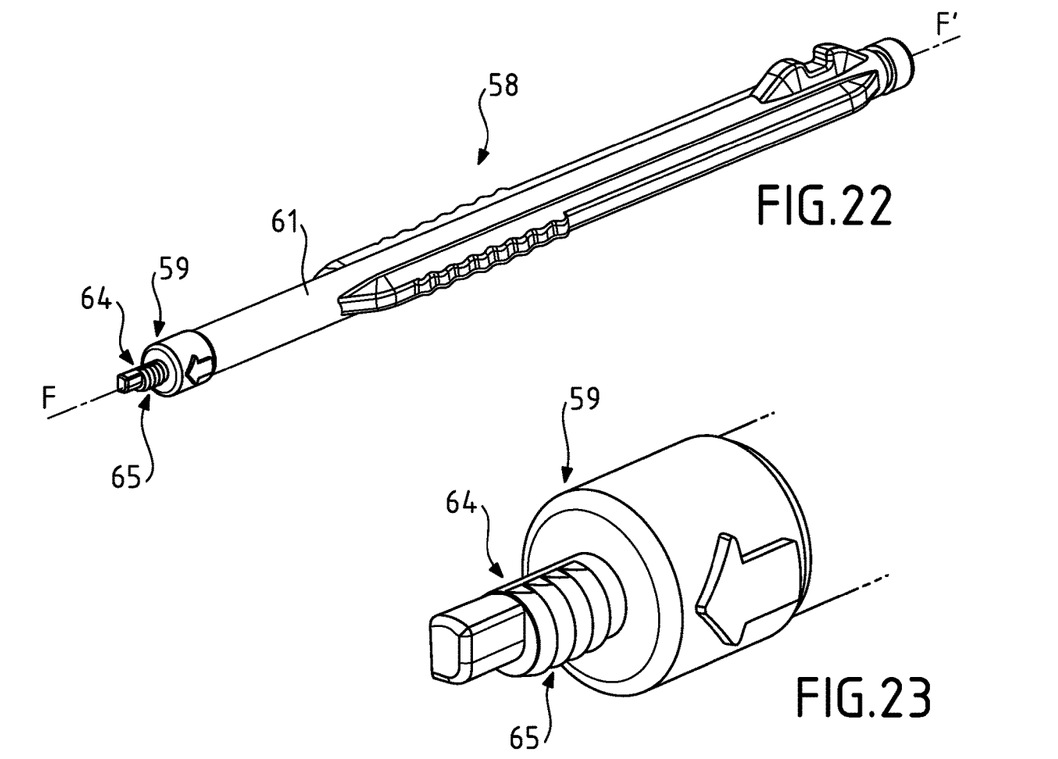
FIG. 22 illustrates, according to a perspective view, the second gripping instrument of the kit of the invention, provided with a second endpiece for securing the secondary component of an implant in accordance with the invention.
FIG. 23 illustrates, according to a perspective view, the second endpiece of this second instrument.
Figure 24:
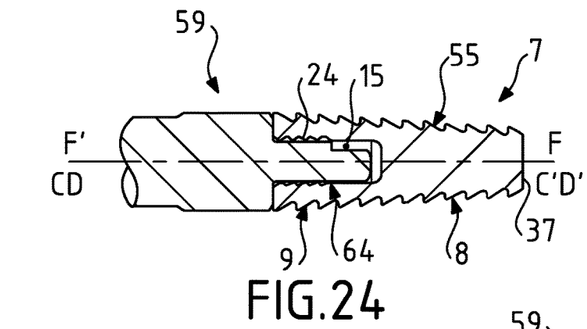
FIGS. 24 and 25 illustrate, according to longitudinal sectional views, unlocked (FIG. 24) and locked (FIG. 25) configurations of the secondary component of an implant in accordance with the invention on the endpiece of FIG. 23.
Figure 25:
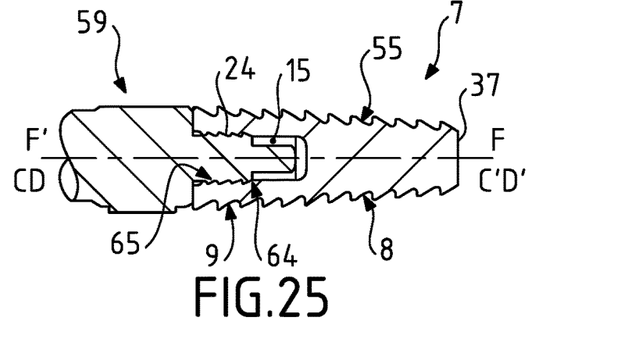

As illustrated in the figures, the implant 1 of the invention comprises two distinct components, designed to be linked to each other. In this instance, the implant 1 comprises a primary component 4 which, in turn, includes a primary anchoring body 5 advantageously designed to ensure the anchoring of the primary component 4 in the first bone 2, and a male connector 6. Preferably, said primary anchoring body 5 and said male connector 6 extend respectively according to first A-A' and second B-B' axes of longitudinal extension. The implant 1 also comprises a secondary component 7 which, in turn, includes a secondary anchoring body 8 advantageously designed to ensure the anchoring of the secondary component 7 in the second bone 3, and a female connector 9. Preferably, said secondary anchoring body 8 and said female connector 9 extend respectively according to third C-C' and fourth D-D' axes of longitudinal extension. Advantageously, said male 6 and female 9 connectors are designed and configured to cooperate by form-fitting, whether in a reversible manner or not, so as to link together said primary 4 and secondary 7 components, preferably by ensuring a direct, robust and reliable mechanical linkage therebetween. In other words, while said primary 4 and secondary 7 components of the implant 1 may be advantageously implemented separately, for example in a sequential manner, during the same surgical operation of setting the implant 1 in the body of a patient, the primary 4 and secondary 7 components are yet provided to be in fine linked together via the male 6 and female 9 connectors (FIG. 1). Thus, the first bone 2 and the second bone 3 are linked to each other by the implant 1, once said primary 4 and secondary 7 components are linked together, and advantageously secured, via their respective male 6 and female 9 connectors (FIGS. 9 and 17).

Preferentially, each of the primary 4 and secondary 6 components forms an integral part made in one piece, the primary 5 and secondary 7 anchoring bodies being respectively integral with the male 6 and female 9 connectors. Such a design allows conferring the primary 4 and secondary 7 components with a good structural resistance while facilitating their manufacture, for example through molding and/or machining operation(s), without requiring any step of assembling attached parts. Alternatively, said primary 4 and secondary 7 components may result on the contrary from the assembly of several parts, and not be integral. Advantageously, the primary 4 and secondary 7 components may be made of one single material. Preferably, both of the primary 4 and secondary 7 components are thus made of a polymer material, for example of polyetheretherketone PEEK.

Indeed, such a material is interesting in that it is biocompatible, radio-transparent, light and inexpensive to implement. Alternatively, the primary 4 and secondary 6 components may be made of another material, for example a metallic material such as stainless steel or titanium.

Figures 2, 3, 4, 5:
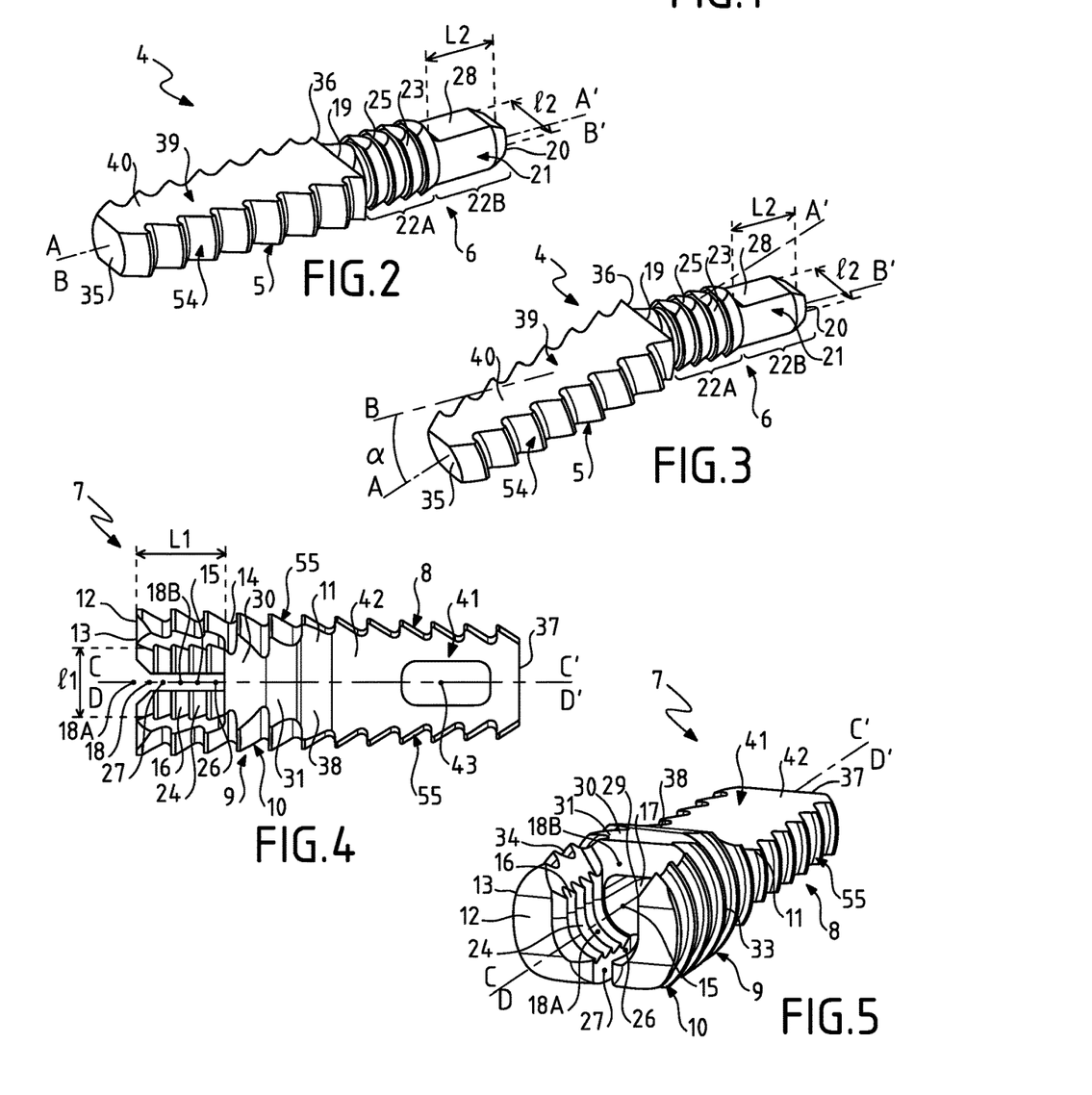
FIGS. 2 and 3 respectively illustrate, according to perspective views, two variants of the primary component of the implant of FIG. 1.
FIGS. 4 to 6 respectively illustrate top, perspective and longitudinal sectional views of the secondary component of FIG. 1.
Figure 6:
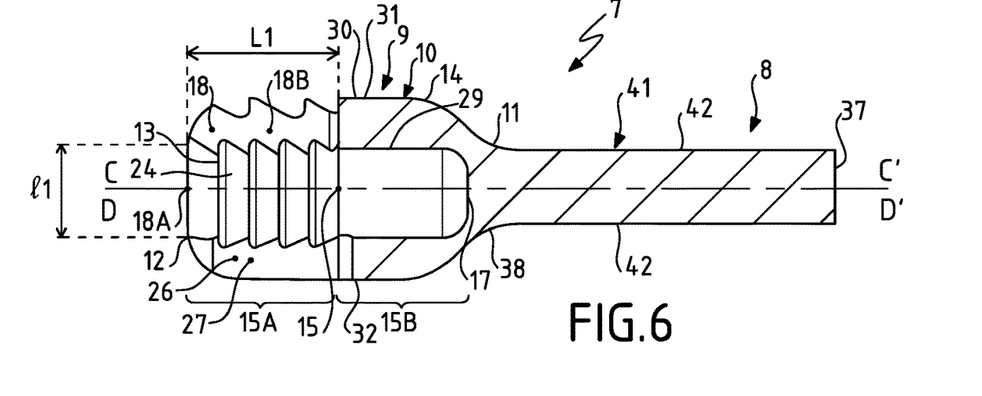
Figures 7, 8:
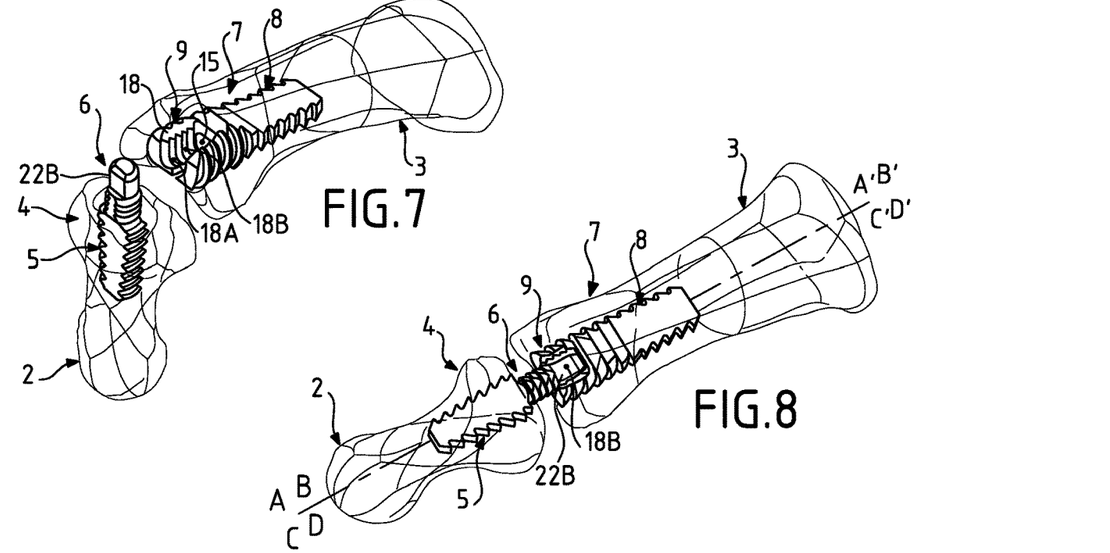
FIGS. 7 to 9 illustrate, according to perspective views, successive steps of a preferred implementation of the implant of FIG. 1.

According to the invention, the female connector 9 comprises a main body 10 which extends longitudinally between a rear end 11 linked to the secondary anchoring body 8 and an opposite front face 12, which is preferably delimited by a peripheral front edge 13. Preferably, the main body 10 extends longitudinally along the fourth axis of extension D-D' of the female connector 9. The main body 10 has a lateral wall 14, which links said rear end 11 and said front face 12. Preferably, this lateral wall 14 is cylindrical or has a generally convergent shape (for example conical), from the front face 12 in the direction of the rear end 11, along the fourth axis D-D'. Preferably, the front face 12 extends in a plane substantially orthogonal to the fourth axis D-D'. By «general shape» is meant the overall external shape of the concerned element, excluding any possible flattened portions, chamfers, teeth, and other protruding or recessed elements. As illustrated in FIGS. 4 to 6, the female connector 9 comprises a housing 15, which is formed within said main body 10 and which is configured to receive the male connector 8 in order to link together (that is to say in order to connect, couple together) the primary 4 and secondary 7 components. Advantageously, the housing 15 forms a hollow space, defined by an internal wall 16, inside the main body 10, and with shapes and dimensions matching with the respective ones of the male connector 6. Thus, the housing 15 is advantageously configured and sized to receive therewithin at least one portion, and preferably the entirety of the male connector 6. Preferably, the housing 15 extends longitudinally according to a parallel direction, and more preferably, coincident with the fourth axis of extension D-D' of the female connector 9. Preferably, the housing 15 extends from the front face 12 up to an opposite bottom wall 17, which is advantageously positioned in the immediate vicinity of the rear end 11 of the main body 10. Still preferably, the housing 15 includes two distinct portions along the fourth axis D-D', in this instance a first portion 15A which extends from said front face 12, and a second portion 15B which prolongs the first portion 15A up to said bottom wall 17 (FIG. 6).

According to the invention, the female connector 9 further comprises an opening 18 which is formed in said main body 10, which opening 18 is in communication (advantageously direct communication) with said housing 15, that is to say that it provides access to the latter from the external environment to the main body 10. According to the invention, the opening 18 extends continuously on both said front face 12 and said lateral wall 14. Advantageously, the opening 18 of the female connector 9 comprises a first opening area 18A, which extends on said front face 12, and a second opening area 18B, which is contiguous to the first area 18A, immediately prolongs the latter and extends over at least one portion of said lateral wall 14. In general, the opening 18 is sized and configured to enable a lateral introduction of the male connector 6 (or of at least one portion of the latter) into said housing 15 via said opening 18. In particular, this means that the configuration, the shaping and the dimensions of the second area 18B of the opening 18 are advantageously chosen in consideration of the specific configuration, shaping and dimensions of the male connector 8, so that at least one portion (for example an end free portion) of the latter could be introduced into said housing 15 via said second opening area 18B. Advantageously, the housing 15 opens from the main body 10 at the level of the front face 12 of the latter via said first opening area 18A, and the latter is preferably sized, shaped and configured to enable a facial introduction of the male connector 6, and preferably of the entirety of the latter, into said housing 15 via the first area 18A. Thus, the female connector 9 is advantageously capable of receiving, at least partially, the male connector 6 within its housing 15 via both the first area 18A and the second area 18B of its opening 18.

Preferably, the introduction of the male connector 6 into the housing 15 via the sole second area 18B of the opening 18 does not allow linking together the primary 4 and secondary 7 components in a complete and satisfactory manner. Indeed, when the primary 4 and secondary 7 components are linked together, said male connector 6 is preferably housed, at least partially, into the housing 15 so that its second axis of extension B-B' is coincident with the fourth axis D-D'. In contrast, it is still advantageously possible to obtain a full cooperation of the male 6 and female 9 connectors by introducing at least one portion of the male connector 6 into said housing 15 only via the first area 18A of the opening 18.

The shaping, the configuration and the sizing of this female connector 9, and in particular of its housing 15 and of its opening 18, will be better understood in relation with the following description of the male connector 6. Preferably, the male connector 6 is in the form of an elongate body, and preferably extends longitudinally between a first end 19 linked (directly or indirectly) to the primary anchoring body 5 and an opposite second free end 20, along the second axis B-B' (FIGS. 2 and 3). The second free end 20 of the male connector 6 is advantageously chamfered so as to facilitate its introduction within the housing 15 of the female connector 9. The first end 19 of the male connector 6 forms in turn preferably a point of attachment of the male connector 6 with the primary anchoring body 5. Preferably, the male connector 6 has an outer surface 21, which links the first end 19 to the second free end 20 of the male connector 6, and forms for example a substantially solid and massive body, delimited by said outer surface 21. As illustrated, the latter is preferably of a cylindrical shape with a circular base. Thus, the male connector 6 is advantageously in the form of a cylindrical rod with a substantially circular section (orthogonal to said second axis B-B'). Nonetheless, other shapes may be considered and said outer surface 21 may, for example, be of a cylindrical shape with a polygonal base (for example with a hexagonal base). Still alternatively, the outer surface 21 may be assigned a generally convergent (for example conical) shape in the direction of the second free end 20 of the male connector 6. Advantageously, the male connector 6 comprises a first portion 22A and a second portion 22B, the first portion 22A extending from the first end 19, whereas the second portion 22B prolongs the first portion 22A up to said second free end 20. Thus, the second portion 22B forms an end (or distal) portion of the male connector 6, advantageously intended to be introduced within the housing 15 of the female connector 9 before the first portion 22A. Considering the foregoing, these first 22A and second 22B portions may have an average section identical or not. Advantageously, the first portion 22A is provided to be received, at least partially, into the first portion 15A of said housing 15, whereas the second portion 22B is provided to be received, at least partially, into the second portion 15B of said housing 15, when the primary 4 and secondary 7 components are linked together.

Consequently, the housing 15 of the female connector 9 is then preferably in the form of a hollow space defined by a cylindrical internal wall 16, and with a shape complementary to the cylindrical general shape with a circular base of the outer surface 21 of the male connector 6. Considering the foregoing, the first 15A and second 15B portions of the housing 15 may have an average section identical or not. In this manner, the male connector 6 may fit tightly (possibly with a very slight clearance in order to facilitate the relative assembly of the primary 4 and secondary 7 components) into said housing 15. Still preferably, the housing 15 extends longitudinally over a length substantially close to the length of the male connector 8 (measured from the first end 19 up to the second free end 20 of the latter). However, as will be seen later, it is optionally conceivable that the housing 15 extends longitudinally over a length smaller than the length of the male connector 6.

Preferably, the second area 18B of the opening 18 is shaped, configured and sized to enable a lateral introduction of the second portion 22B of the male connector 6 into the housing 15 via the second area 18B of the opening 18. The second area 18B is then preferably, as illustrated in the figures, in the form of a substantially rectangular window, and extends longitudinally, from the front edge 13 and in the direction of the rear end 11 of said main body 10, according to a direction substantially parallel to the fourth axis of extension D-D' of the latter. In other words, the second area 18B of the opening 18 preferably extends axially opposite the housing 15, over at least one portion of the length of the latter. Advantageously, the second area 18B extends longitudinally over a length L1 of the main body 10 substantially equal to (or close to) the length L2 of the second portion 22B of the male connector 6, and in any case over a length L1 preferably smaller than the total length of the male connector 6. Preferably, the second area 18B of the opening 18 extends transversely over a width l1 at least equal to (and preferably very slightly greater than) the maximum transverse bulk l2 of the second portion 22B of the male connector 6. This means in particular that the width l1 (preferably considered according to a direction orthogonal to the fourth axis D-D') of the second area 18B is at least equal to (and preferably very slightly greater than) the diameter of the second portion 22B of the male connector 6 (when the latter is of a cylindrical shape with a circular base), or the diameter of the circle in which is inscribed the polygonal section of the male connector 6 (when the outer surface 21 of the latter has a generally cylindrical shape with a polygonal base). Advantageously, the respective edges of the first 18A and second 18B areas of the opening 18 are chamfered or flared so as to facilitate the introduction of the male connector 6, in particular of its second portion 22B, into the housing 15 of the female connector 9 (FIGS. 4 to 6).

Considering the foregoing, it is understood that the male connector 6 may be advantageously introduced into the housing 15 of the female connector 9 through a combination of a displacement according to a direction substantially orthogonal to the respective second B-B' and fourth D-D' axes of longitudinal extension of the male 6 and female 9 connectors, and of a displacement according to a direction substantially coincident with these same second B-B' and fourth D-D' axes. Thus, the primary 5 and secondary 8 anchoring bodies being respectively anchored in the first bone 2 and in the second bone 3, one portion at least of the male connector 8 (in this instance, at last its second end portion 22A) may be introduced laterally into the housing 15 of the female connector 9, without being necessary to space apart the first 2 and second 3 bones beforehand by a distance at least equal to the total length of the male connector 8 according to the second axis B-B'. Consequently, the surgeon who implements the implant 1 of the invention in the body of a patient may advantageously anchor one and then the other said primary 4 and secondary 7 components respectively in the first 2 and second 3 bones, then link together the primary 4 and secondary 7 components via their respective male 6 and female 9 connectors, while keeping a particularly narrow distance between the first 2 and second 3 bones. Thus, the interarticular distraction necessary to the implementation of the implant 1 of the invention is particularly limited, which advantageously allows limiting the harmful effects of the surgery on the tendons and other surrounding soft tissues.

Preferably, the male 6 and female 9 connectors respectively comprise complementary first and second locking means which cooperate so as to ensure the relative locking of the primary 4 and secondary 7 components, once the latter are linked, that is to say once the male connector 6 is introduced within the housing 15 of the female connector 9 (preferably coaxially with said housing 15). In other words, the male connector 6 carries a first locking means, for example at the level of its outer surface 21 or its second free end 21, designed to cooperate with a corresponding second locking means carried by the female connector 9, for example at the level of the inner wall 16 of its housing 15, in order to avoid, or at least strongly limit, any risk of inadvertent dissociation of the primary 4 and secondary 6 components, once the latter are linked together. In particular, these complementary locking means are advantageously designed to prevent, or at least strongly limit, any relative displacement of the primary 4 and secondary 7 components according to a direction parallel to the respective second B-B' and fourth D-D' axes of extension of the male 6 and female 9 connectors, once the primary 4 and secondary 6 components are linked together via the latter.

Said first and second locking means may be of any type known in the prior art, and be designed to ensure a relative locking of the primary 4 and secondary 6 components for example by bonding, screwing, clipping, snap-fitting or still by forced fitting. Preferably, as illustrated in the figures, the locking is ensured by snap-fitting, the first and second locking means being respectively formed for example by at least one tooth 23 which protrudes from the outer surface 21 of the male connector 6, and by at least one complementary notch 24 formed in the inner wall 16 of the housing 15 of the female connector 9. The cooperation of the tooth 23 and of the notch 24 may be then advantageously promoted by elastic deformation of the tooth 23, and/or of the notch 24, and/or still of the lateral wall 14 of the main body 10 of the female connector 9.

According to a preferred variant, the implant 1 is advantageously intended to be left in the body of the patient upon completion of the surgery, for the entire life of said patient. In this case, the first and second locking means are advantageously designed and configured to ensure a definitive (or at least hardly reversible without exerting considerable forces) relative locking of the primary 4 and secondary 7 components. Preferably, the first locking means is then formed by at least one tooth 23 (or lug, or still boss) which protrudes from the outer surface 21 of the male connector 8 all around the circumference of the section of the latter, whereas the second locking means may be formed by at least one complementary notch 24 (or cutout, or still depression) formed in the inner wall 16 of the housing 15 of the female connector 9 all around the circumference of the section of said housing 15. Advantageously, each of the tooth 23 and the corresponding notch 24 may present an inclined face and opposite right face matched with each other, the cooperation of the inclined faces promoting the snap-fitting of the tooth 23 into the notch 24, whereas the cooperation of the right faces resists, once the tooth 23 snap-fits into the notch 24, the relative disengagement of said tooth and notch. Alternatively, said locking means may be formed or replaced by a glue introduced into the housing 15, which ensures a strong adhesion between the outer surface 21 of the male connector 6 and the inner wall 16 of the housing 15 of the female connector 9.

According to another preferred variant, the implant 1 may be, on the contrary, provided to enable its future ablation, that is to say to enable its total or partial extraction from the body of the patient (extraction of one or both of the primary 4 and secondary 7 components), or at least to enable the disconnection and the separation of the primary 4 and secondary 7 components. To this end, the complementary first and second locking means will be preferably designed and configured to ensure a reversible relative locking of the primary 4 and secondary 7 components, so that the unlocking and the separation of the latter are made possible. For example, such reversible locking means may be formed respectively by at least one tooth 23 (or lug, or still boss) which punctually protrudes from the outer surface 21 of the male connector 6, and by at least one complementary notch 24 (or cutout, or still depression) formed punctually in the inner wall 16 of the housing 15 of the female connector 9. Thus, a slight rotation of the male connector 6 in the female connector 9 according to the second axis B-B' may be sufficient to disengage said tooth 23 and said notch 24 and to enable the decoupling of the primary 4 and secondary 7 components.

Preferably, the first and second locking means are more specifically designed and configured to enable a relative unlocking of the primary 4 and secondary 7 components through a quarter-turn rotation of the male connector 6 in the female connector 9 according to the second axis of extension B-B' of the male connector 6. Thus, it is possible to obtain a reversible and effective locking, while avoiding any risk of inadvertent unlocking of the male 6 and female 9 connectors, in particular under the effect of an unintentional slight relative rotation of the first 2 and second 3 bones. For example, as illustrated in the figures, the first locking means may be advantageously formed on the one hand, by at least one tooth 23 (or lug, or still boss) which protrudes from the outer surface 21 of the male connector 6 along the entire circumference of the section of the latter and, on the other hand, by two flattened portion 25 formed axially, according to the second axis of extension B-B' of the male connector 6, into and through the tooth 23 and positioned parallel to each other, on either side of the second axis B-B'. The second locking means may be in turn advantageously formed on the one hand, by at least one notch 24 (or cutout, or still depression) complementary to said tooth 23, and formed in the inner wall 16 of the housing 15 of the female connector 9 along the entire circumference of the section of the housing 15 and, on the other hand, by two grooves 26 with sizes matching with those of the flattened portions 25 of the first locking means, these grooves 26 being formed axially, according to the fourth axis of extension D-D' of the female connector 9 and of its main body 10, in and through the notch 24 and being positioned parallel to each other on either side of the fourth axis D-D'. Thus, a quarter-turn rotation of the male connector 6 in the female connector 9 according to the second axis of extension B-B' of the male connector 6 will advantageously result in mating the flattened portions 25 and the corresponding grooves 26, thereby enabling the release of the tooth 23 from the corresponding notch 24. Advantageously, the tooth 23 and the notch 24 may respectively present an inclined face and an opposite right face, as mentioned before, so as to obtain a reversible, robust and reliable locking. Preferably, at least one of the grooves 26 may be aligned and centered on the second area 18B of the opening 18 of the female connector 9. In this case, the considered groove 26 will be advantageously formed, over at least one portion of its length, by said second area 18B.

Preferably, and as illustrated in the figures, the complementary first and second locking means are respectively formed by a plurality of teeth 23 (or lugs, or still bosses) aligned according to the second axis of extension B-B' of the male connector 6, and by a plurality of notches 24 (or cutouts, or still depressions) aligned according to the fourth axis of extension D-D' of the female connector 9 and of its main body 10. Thus, the first and second locking means advantageously form a system of complementary staggered teeth 23 and notches 24 (or at least one notch 24) enabling a progressive adjustment of the relative spacing of the primary 5 and secondary 8 anchoring bodies. Indeed, the male connector 6 being introduced within the housing 15 of the female connector 9, preferably so that the male connector 6 extends coaxially with the housing 15, an axial translation of the male connector 6 in the housing 15 then advantageously allows engaging the locking means, and thereby locking the primary 4 and secondary 7 components, according to a plurality of axial positions, which correspond to a more or less significant spacing of the primary 5 and secondary 8 anchoring bodies to which are respectively linked the male 6 and female 9 connectors. Thus, after having introduced and anchored the primary 4 and secondary 7 components respectively into the first bone 2 and into the second bone 3, the surgeon may advantageously link together the primary 4 and secondary 7 components and lock them to each other according to a first position corresponding to a first relative spacing of their respective anchoring bodies, then progressively bring the first 2 and second 3 bones close to each other until joining them, while keeping a relative locking of the primary 4 and secondary 7 components.

As illustrated in FIGS. 4 to 6, said female connector 9 may optionally and advantageously comprise a slot 27 formed in the lateral wall 14 of the main body 10 of the female connector 9, in communication with the housing 15 of the latter. Preferably, this through slot 27 is positioned opposite the opening 18 and, still more specifically, opposite the second area 18B of the latter. Advantageously, the slot 27 extends axially according to the fourth axis D-D', from the front face 12 (from which it preferably opens) in the direction of the rear end 11 of the main body 10, and preferably parallel to the second area 18B of the opening 18. Preferably, the slot 27 extends over at least one portion of the length of said main body 10 and, still more preferably, over a length substantially close to the length L1 of said second area 18B. Thus, such a slot 27 advantageously allows facilitating a preferably elastic deformation of the main body 10 (and in particular of its lateral wall 14) during the relative locking of the primary 4 and secondary 7 components, and/or during the adjustment of the relative spacing of the respective primary 5 and secondary 8 anchoring bodies of the latter. It is then particularly possible to manually adjust, with a sufficient but still moderate force, the relative spacing of the primary 5 and secondary 8 anchoring bodies, and therefore of the first 2 and second 3 bones that are intended to be merged together.

Advantageously, and as shown in FIGS. 2 and 3 and 10 to 13, the first locking means is carried by the first portion 22A of the male connector 6 only. Thus, the second end portion 22B of the male connector 6 is advantageously devoid of any first locking means. In this manner, it is possible to introduce the second portion 22B of the male connector 6 into the housing 15 via the opening 18, and thereby link the primary 4 and secondary 7 components yet without locking them to each other. The relative locking of the primary 4 and secondary 7 components will then be possible only when the first portion 22A of the male connector 6 will be, in turn, introduced into the housing 15 of the female connector 9. Such a design proves to be practical and interesting, in particular in the case where the complementary locking means are not designed to ensure a reversible relative locking of the primary 4 and secondary 7 components, since the surgeon can then carry out partial relative assembly tests of the latter, yet without the risk of locking them immediately and irreversibly. Moreover, in such a case, the corresponding second locking means may be advantageously respectively carried only or mostly by the first portion 15A of the housing 15, which will allow facilitating the design and the manufacture of the secondary component 7.

Preferably, the male 6 and female 9 connectors comprise respectively complementary first and second blocking means which cooperate so as to limit or prevent the rotation of the male connector 6 relative to the female connector 9, when the male connector 6 is in place in the housing 15 of the female connector 9, and in particular in the case considered hereinbefore where the male connector 8 and the housing 15 are generally of a cylindrical shape with a circular base. When the implant 1 is placed at the level of the first 2 and second 3 bones, such blocking means thus advantageously contribute to limiting or preventing the rotation of the first bone 2 and of the second bone 3 relative to each other. Thus, the implant 1 advantageously allows immobilizing the latter both in translation and in rotation relative to each other, which promotes their osseous fusion and therefore enables a rapid arthrodesis. For example, such complementary first and second blocking means may be respectively formed by first 28 and second 29 longitudinal axial flattened portions, respectively formed in the outer surface 21 of the male connector 6 and in the inner wall 16 of the housing 15, preferably only at the level of the second portion 22B of the male connector 6 and of the second portion 15B of the housing 15 of the female connector 9. Possibly, such rotation blocking means may serve as a mistake-proofing system, which limits the possible cooperation configurations of the male 6 and female 9 connectors (in particular in the case where the primary component 4 is bent, as described later on).

Preferably, the female connector 9 will be provided with at least one longitudinal axial flattened portion 30, and preferably with two longitudinal axial flattened portions 30, formed in its lateral wall 14, and which preferably extend from the front edge 13 up to the rear end 11 of its main body 10 according to the fourth axis D-D' (FIGS. 4 and 5). Advantageously, these flattened portions 30 are positioned parallel to each other on either side of the fourth axis D-D'. The female connector 9 being preferably intended to be introduced into the second bone 3, such flattened portions 30 advantageously contribute to blocking the female connector 9 in rotation in the second bone 3 according to the fourth axis D-D'. Still more advantageously, one 34 of said flattened portions 30 is aligned and centered longitudinally with the second area 18B of the opening 18. The other of said flattened portions 30 is in turn advantageously aligned and centered longitudinally on the optional slot 27. As in particular seen from FIG. 5, the main body 10 of the female connector 9 then presents preferably a section (orthogonal to said fourth axis D-D') with two substantially rectilinear and parallel opposite sides, the two other sides being substantially curvilinear. In a particularly preferred manner, the main body 10 thus comprises a first face 31 called dorsal, carrying the second area 18B of the opening 18 and one of the flattened portions 30, an opposite second face 32 called ventral, carrying said optional slot 27 and the other of the flattened portions 30, and third 33 and fourth 34 lateral faces, opposite to each other and linking said dorsal 31 and ventral 32 faces.

The respective primary 5 and secondary 8 anchoring bodies of the primary 4 and secondary 7 components of the implant 1 of the invention will now be described in detail hereinafter. Of course, the following description is not restrictive, and embodiments and variants other than those disclosed hereinafter may be considered without departing from the scope of the invention. Preferably, the primary anchoring body 5 is intended to be completely inserted into the first bone 2, whereas the male connector 6 is provided to protrude out of the first bone 2, when the primary component 4 is in place in the latter. Respectively, the secondary anchoring body 8 is preferably provided to be completely inserted into the second bone 3, the female connector 9 being advantageously in turn provided to be completely inserted into the latter (and therefore not to protrude out of the second bone 3), when the secondary component 7 is in place in the second bone 3 (FIGS. 7 to 9 and 15 to 17).

Preferably, the primary 5 and secondary 8 anchoring bodies are respectively designed to ensure the insertion and anchoring of the primary component 4 into the first bone 2, and of the secondary component 7 into the second bone 3, by impaction or by forced wedging, so that said components 4, 7 could preferably be inserted and anchored into the corresponding bones 2, 3 according to a mere translational movement. As such, said primary 5 and secondary 7 anchoring bodies respectively are then preferably devoid of any means for screwing the primary anchoring body 5 in the first bone 2 and the secondary anchoring body 8 in the second bone 3. Such a design is particularly advantageous, in particular in the case where each of the primary 4 and secondary 6 components forms an integral part made in one piece. Indeed, the insertion and the anchoring of the primary component 4 into the first bone 2, and of the secondary component 7 into the second bone 3 by impaction or by forced wedging advantageously allow ensuring a perfect control of the final orientation of the primary 4 and secondary 7 components. In particular, this allows ensuring a perfect control of the relative orientation of the respective male 6 and female 9 connectors of the primary 4 and secondary 7 components, respectively about the second B-B' and fourth D-D' axes of longitudinal extension, during the implantation of the latter in the body of the patient. Hence, a perfect alignment of the male connector 6 with the opening 18 of the female connector 9, and in particular with the second opening area 18B of said opening 18, is thus advantageously facilitated. The relative assembly of the primary 4 and secondary 7 components, once the latter are implanted in the body of the patient, is thus advantageously facilitated. Preferably, the primary anchoring body 5 is intended to be inserted and anchored into a medullary canal of the first bone 2, whereas the secondary anchoring body 8 is respectively intended to be inserted and anchored into a medullary canal of the second bone 3. In this case, the primary 5 and secondary 8 anchoring bodies may be implanted in the medullary canals of the first 2 and of the second 3 bones, for example after the end of the concerned bone (formed for example by an cartilaginous end surface) has been pierced or removed in order to form an access opening to said medullary canal. Preferably, the internal osseous stock of said medullary canals must also be adapted to allow accommodating the primary anchoring body 5, respectively the secondary anchoring body 8. Of course, without departing from the scope of the invention, the primary anchoring body 5 and/or the secondary anchoring body 8 may be designed to be anchored in any other portion of said first 2 and second 3 bones, and for example to be anchored in an orifice formed beforehand in the cortical portion of the latter. In the preferred case where the implant 1 preferably forms an intramedullary implant, the primary 5 and secondary 8 anchoring bodies are advantageously shaped and configured to be able to be inserted axially into the respective medullary canals of the first 2 and second 3 bones. In particular, the medullary canal of such bones being generally tubular shaped, substantially cylindrical, the primary 5 and secondary 8 anchoring bodies preferably have an elongate and axial general shape, and preferably cylindrical, conical, or still prismatic, and will be shaped so as to be inserted coaxially within the concerned medullary canal (FIGS. 7 to 9 and 15 to 17).

In general, the primary anchoring body 5 preferably extends longitudinally along the first axis A-A' between a primary end 35 for penetrating into the first bone 2 and an opposite primary base end 36. The primary penetrating end 35 forms a first free end of the implant 1, whereas the opposite primary base end 36 preferably forms a point of attachment of the primary anchoring body 5 with the male connector 6. Respectively, the secondary anchoring body 8 extends longitudinally along the second axis B-B' between a secondary end 37 for penetrating into the second bone 3 and an opposite secondary base end 38. The secondary penetrating end 37 forms a second free end of the implant 1, whereas the opposite secondary base end 38 preferably forms a point of attachment of the secondary anchoring body 8 with the female connector 9.

According to a first preferred embodiment of the implant 1 of the invention (FIGS. 1 to 9), the primary anchoring body 5 has a primary outer surface 39, which links the primary base end 36 to the primary penetrating end 35, and forms for example a substantially solid and massive body, delimited by said primary outer surface 39. Preferably, the primary penetrating end 35 is slender, conical, cambered or chamfered so as to facilitate its insertion and its penetration into the first bone 2. As illustrated, the primary outer surface 39 preferably has a generally convergent shape (for example conical), in the direction of the primary penetrating end 35, along the first axis A-A'. In particular, such a shaping allows promoting the wedging (for example forced wedging) of the primary anchoring body 5 in the first bone 2, the primary anchoring body 5 thus being able to adapt to medullary canals with different diameters. Preferably, the primary anchoring body 5 is provided with at least one longitudinal primary flattened portion 40 formed in the primary outer surface 41. Advantageously, this primary flattened portion 40 extends according to the first axis A-A', preferably from said primary penetrating end 40 up to said opposite primary base end 41 (FIGS. 1 to 3). Still more preferably, the primary anchoring body 5 is provided with two longitudinal primary flattened portions 40 formed in the primary outer surface 39. Preferably, both of these primary flattened portions 40 extend according to the first axis A-A', from said primary penetrating end 35 up to said opposite primary base end 36. Advantageously with identical shapes and dimensions, the primary flattened portions 40 are preferably positioned parallel to each other on either side of the first axis A-A'. As illustrated, the primary anchoring body 5 may thus advantageously be in the form of a body or of a plate with a substantially trapezoidal profile, and with a substantially rectangular or trapezoidal section. The presence of such a primary flattened portion 40 (and preferably of two primary flattened portions 40) advantageously promotes a good adaptation to the osseous anatomy of the patient, while preferably contributing to preventing the rotation of the primary component 4, once the latter is anchored in the medullary canal of the first bone 2.

In a similarly advantageous manner, the secondary anchoring body 8 preferably has a secondary outer surface 41, which links the secondary base end 38 to the secondary penetrating end 37, and forms for example a substantially solid and massive body, delimited by said secondary outer surface 41 (FIGS. 4 and 5). As illustrated, the secondary outer surface 41 preferably has a generally convergent shape (for example conical), in the direction of the secondary penetrating end 37, along the second axis B-B'. Advantageously, when the secondary anchoring body 8 and the female connector 9 form an integral part made in one piece, the secondary outer surface 41 of the secondary anchoring body 8 advantageously prolongs the lateral wall 14 of the female connector 9.

Preferably, the secondary anchoring body 8 is provided with at least one longitudinal secondary flattened portion 42 formed in said secondary outer surface 41 of the secondary anchoring body 8. Advantageously, as illustrated in FIGS. 4 and 5, said secondary flattened portion 42 extends according to the second axis B-B', preferably from said secondary penetrating end 37 up to said opposite secondary base end 38. Still more preferably, the secondary anchoring body 7 is provided with two longitudinal secondary flattened portions 42 formed in said secondary outer surface 41 (FIG. 6). Both of these secondary flattened portions 42 then preferably extend according to the second axis B-B', from said secondary penetrating end 37 up to said opposite secondary base end 38. Advantageously with identical shapes and dimensions, these secondary flattened portions 42 are preferably positioned parallel to each other on either side of the second axis B-B'. As illustrated, the secondary anchoring body 8 may thus advantageously be in the form of a body with a substantially trapezoidal profile, and with a substantially rectangular or trapezoidal section. The presence of such a secondary flattened portion 42 (and preferably two secondary flattened portions 42) advantageously promotes a good adaption to the osseous anatomy of the patient, while preferably contributing to preventing the rotation of the secondary component 8, once the latter is anchored in the medullary canal of the second bone 3. Advantageously, the secondary anchoring flattened portion(s) 42 is(are) arranged so as to axially prolong (or at least to be axially aligned with) the respective flattened portion(s) 30 of the main body 10 of the female connector 9 (FIGS. 4 and 5).

According to this first preferred embodiment of the implant 1 of the invention, the primary 5 and secondary 8 anchoring bodies are preferably substantially rigid and non-deformable (or only in a very limited and localized manner), so that they are not significantly deformed by the respective action of the first 2 and second 3 bones. In particular, the primary 5 and secondary 8 anchoring bodies are designed (in particular in terms of sizing and materials selection) so as not to bend over respectively along the first A-A' and second B-B' axes, or not to contract by the effect of an axial or radial pressure, when they are respectively introduced, and possibly anchored, into the first 2 and second 3 bones. This being so, the secondary anchoring body 8 may nonetheless be optionally provided with a perforation 43 formed through the secondary outer surface 41 (FIG. 4). Opening on either side of said secondary outer surface 41, and preferably through the secondary flattened portion(s) 42, this perforation 43 preferably extends longitudinally along the second axis B-B'. Depending on the dimensions and positions selected for such a perforation 43, it is then possible to confer the secondary anchoring body 8 with some deformability (in particular by the effect of a radial pressure), for example in order to facilitate its insertion and its anchoring into the second bone 3. Besides, such a perforation 43 may advantageously enable the formation of an osseous bridge through the secondary anchoring body 8 during the arthrodesis, thereby promoting a robust and reliable anchoring of the secondary anchoring body 8 in the second bone 3. Of course, the primary anchoring body 5 may, optionally or alternatively, be provided with such a perforation.

According to a second preferred embodiment of the implant 1 of the invention (FIGS. 10 to 17), the primary anchoring body 5 comprises at least two primary anchoring arms 44, 45, 46, which extend from the vicinity of the primary base end 36 in the direction of the primary penetrating end 35 of the primary anchoring body 5. Preferably, these primary anchoring arms 44, 45, 46 are orientated according to their respective specific directions, getting away from said primary base end 36. In this case, the first axis A-A' then corresponds to the average general direction of extension of the primary anchoring body 5, resulting from the combination of the primary anchoring arms 44, 45, 46. Advantageously, each of the latter has a terminal end 47, 48, 49 for implantation in the first bone 2. Preferably slender, conical, cambered or chamfered in order to facilitate the insertion and the penetration of the primary anchoring arms 44, 45, 46 into the first bone 2, these terminal ends 47, 48, 49 advantageously define the primary penetrating end 35 of the primary anchoring body 5. Advantageously, said primary anchoring arms 44, 45, 46 are designed to be flexible, for example elastically. Thus, the primary anchoring body 5 adapts, by deformation of the primary anchoring arms 44, 45, 46, to the shape of the first bone 2, and in particular of its medullary canal, in order to be able to be anchored in a reliable, safe, painless manner to the patient. Preferably, the primary anchoring arms 44, 45, 46 are separated from each other by a primary free space E so as to be able to be brought close to each other by deformation of the primary anchoring arms 44, 45, 46 by the action of the first bone 2. Preferably, such a design makes the anchoring body 5 compressible in a centripetal manner with respect to the first axis A-A'. Preferably, the elasticity of the primary anchoring arms 44, 45, 46 enables the primary anchoring body 5 to apply a centrifugal pressure onto the medullary canal (or in general onto the anchoring housing), which promotes the retention of the primary component 4 within the first bone 2. Thus, the primary anchoring body 5 is capable of forming a reliable and versatile linkage, of the primary component 4 with the first bone 2. Preferably, each of said primary anchoring arms 44, 45, 46 has an internal side forming a face orientated in the direction of the first axis A-A' and substantially orthoradial with respect to the latter, an opposite external side, and two lateral sides linking the external side to the internal side. Still preferably, said external side is not orthoradial with respect to the first axis A-A', but rather extends according to a direction secant to the latter, so as to define a fictional shape of the primary anchoring body 5 which is generally convergent in the direction of the primary penetrating end 35 of the latter, along the first axis A-A'.

According to a preferred variant (FIGS. 10 and 12), the primary anchoring body 5 comprises two primary anchoring arms 44, 45. Preferably, these primary anchoring arms 44, 45 are disposed symmetrically with respect to a plane carried by the first axis A-A'. Preferably, the lateral sides of these primary anchoring arms 44, 45 are parallel to each other, and coplanar in pairs, so that the shape of said primary anchoring arms 44, 45 is partially delimited by two parallel planes common to said primary anchoring arms 44, 45. Thus, the lateral sides advantageously define flattened portions which contribute to blocking the primary component 4 in rotation around the first axis A-A' relative to the first bone 2.

According to another variant of the invention (FIGS. 11 and 13), the primary anchoring body 5 comprises three primary anchoring arms 44, 45, 46, so as to improve the stability of the primary component 4 in the first bone 2. Preferably, two of these primary anchoring arms 44, 45, 46 are advantageously compliant with those of the preferred variant disclosed hereinabove. Advantageously, the third one of said primary anchoring arms 44, 45, 46 will, in turn, be advantageously disposed so that its specific direction is contained in the plane of symmetry of the two other primary anchoring arms 44, 45, 46. Of course, the primary anchoring body 5 may include more primary anchoring arms, and/or present relative configurations different from the latter, yet without departing from the scope of the invention. Optionally, at least one of the primary anchoring arms 44, 45, 46 may present a narrow-section area 50 promoting the deformation of said primary anchoring arm 44, 45, 46 by bending of the latter at the level of said narrow-section area 50, in the direction of or away from another one of said primary anchoring arms 44, 45, 46 (FIGS. 10 to 13). Preferably, this narrow-section area 50 forms an indentation formed in the primary arm 44, 45, 46, in the vicinity of the primary base end 36, the indentation being advantageously open on the primary free space E, preferably so that the concerned primary anchoring arm 44, 45, 46 could be bent over at the level of its narrow-section area 50 so as to converge toward another one of the primary anchoring arms 44, 45, 46.

According to this second preferred embodiment of the implant 1 of the invention (FIG. 14), the secondary anchoring body 8 advantageously comprises, in turn, two secondary anchoring arms 51, 52, which extend from the vicinity of the secondary base end 38 in the direction of the secondary penetrating end 37 of the secondary anchoring body 8, and which are preferably separated from each other by a secondary free space E' so as to be able to be brought close to each other by deformation of said secondary anchoring arms 51, 52 by the action of the second bone 2. Advantageously, these two secondary anchoring arms 51, 52 are substantially compliant with the description that has been provided hereinabove of the two primary anchoring arms 44, 45 of the preferred variant of FIGS. 10 and 12, consideration being made to the possible differences in sizing, in particular of their section and their length. Besides, the secondary free space E' may be narrower (or larger) than said primary free space E. Preferably, the lateral sides of these two secondary anchoring arms 51, 52 are parallel to each other, and coplanar in pairs, so that the shape of the two secondary anchoring arms 51, 52 is partially delimited by two parallel planes common to said two secondary anchoring arms 51, 52. Thus, the lateral sides advantageously define flattened portions which contribute to blocking the secondary component 5 in rotation around the third axis C-C' relative to the second bone 3. Of course, the secondary anchoring body 8 may include more secondary anchoring arms, and/or present different relative configurations of the latter, yet without departing from the scope of the invention.

Figure 14:
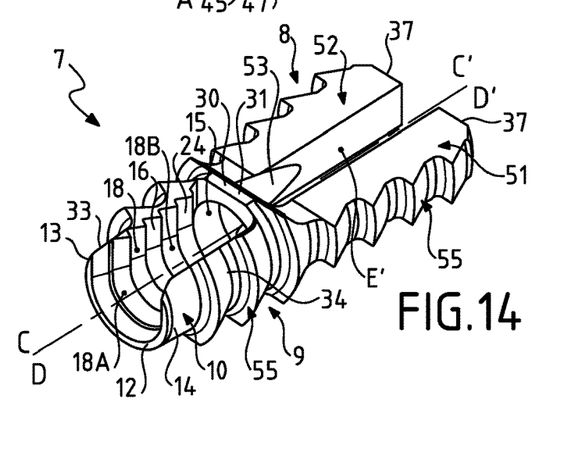
FIG. 14 illustrates, according to a perspective view, a preferred variant of the secondary component of the implant of the invention according to this preferred second embodiment.

FIG. 14 illustrates a particularly interesting preferred variant of this second preferred embodiment of the implant 1 of the invention. According to this preferred variant, the female connector 9 and the secondary anchoring body 8 form an integral part made in one piece, and the housing 15 of the female connector 9 opens at the rear end 11 of the main body 10 of the female connector 9 so as to enable the passage of the male connector 6. In other words, the bottom wall 17 of the housing 15 is advantageously coincident with said rear end 11 and is provided with a through hole (not shown in the figures), and is configured, shaped and sized so as to enable the passage, preferably by translation according to the fourth axis D-D', of the male connector 6 and, sill more specifically, of the second portion 22B of the latter. According to this variant, the housing 15 or the male connector 6 is sized so that at least one portion of said second portion 22B could protrude from the main body 10 via said through hole, when the primary 4 and secondary 7 components are linked together. For this purpose, it is possible for example to provide the length of the housing 15 according to the fourth axis D-D' smaller than the length of the male connector 6 according to the second axis B-B'. Still according to this variant, the secondary free space E' which separates said secondary anchoring arms 51, 52 is advantageously selected with a dimension smaller than the maximum transverse bulk 12 of the second portion 22B of the male connector 6, as defined hereinbefore. Furthermore, at least one of the secondary anchoring arms 51, 52 advantageously present an inclined bearing area 53 promoting the deformation of said secondary anchoring arm 51, 52 by bending of the latter at the level of said inclined bearing area 53, away from another one of said secondary anchoring arms 51, 52, by the action of the male connector 6. As illustrated, the inclined bearing area 53 preferably forms an indentation formed in the secondary arm 51, 52, in the vicinity of the secondary base end 38. Preferably, this indentation has a generally conical shape or at least convergent in the direction of the secondary penetrating end 37 of the secondary anchoring body 8. Furthermore, said indentation is advantageously open on the free space E', preferably so that the concerned secondary anchoring arm 51, 52 could be bent over at the level of its bearing section 53 so as to get away from the other secondary anchoring arm 51, 52, by the action of the free end 21 and of the second portion 22B of the male connector 8 overwhelming the secondary free space E'. Thus, it becomes possible, by coupling the primary 4 and secondary 7 components via the male 6 and female 9 connectors, to force the relative spacing of the secondary arms 51, 52 and in this manner reinforce the anchoring of the secondary component 7 in said second bone 2. Conversely, when the locking means enable a reversible locking of the male 6 and female 9 connectors, the removal of the male connector 8 will advantageously enable the secondary arms 51, 52 to get back toward each other and to release all or part of the anchoring force that they exert in the second bone 3. Henceforth, the secondary component 7 then may be easily extracted from the second bone 3.

Of course, the first and second preferred embodiments disclosed hereinbefore do not necessarily exclude each other, and it is perfectly conceivable that the implant 1 of the invention comprises a primary component 4 according to the first embodiment and a secondary component 6 according to the second embodiment or, conversely, a secondary component 6 according to the second embodiment and a primary component 4 according to the second embodiment.

Moreover, said primary 5 and secondary 8 anchoring bodies are preferably provided respectively with primary 54 and secondary 55 elements for retaining said primary 5 and secondary 8 anchoring bodies respectively in the first 2 and second 3 bones. Possibly deformable by the respective action of the first 2 and second 3 bones, these primary 54 and secondary 55 retaining elements advantageously allow improving the reliability and the robustness of the respective anchoring of the primary 5 and secondary 8 anchoring bodies in the first 2 and second 3 bones.

According to the first preferred embodiment of the implant 1 of the invention, the primary retaining element 54 is formed by at least one row of primary retaining teeth which extend along the primary anchoring body 5 protruding from the primary outer surface 44 of the latter, whereas the secondary retaining element 55 is formed by at least one row of secondary retaining teeth which extend along the secondary anchoring body 8 protruding from the secondary outer surface 41 of the latter. Preferably, in the example of FIGS. 1 to 9, the primary 54 and secondary 55 retaining elements are respectively formed by two rows of primary retaining teeth, each extending along lateral faces of the primary anchoring body 5 which link the faces carrying the primary flattened portions 40, and by two rows of secondary retaining teeth, each extending along lateral faces of the secondary anchoring body 8 which link the faces carrying said secondary flattened portions 42. Preferably, the female connector 9 being intended to be completely inserted into the second bone 3, it is also advantageously provided with a secondary retaining element 55, advantageously formed by at least one row of secondary retaining teeth which extend along the main body 10 protruding from the lateral wall 14 of the latter. Still preferably, the female connector 9 is provided with two rows of secondary retaining teeth, each extending axially respectively along the third 33 and fourth 34 lateral faces of the main body 10 (FIGS. 4 and 5).

According to the second preferred embodiment of the implant 1 of the invention, each of the primary anchoring arms 44, 45, 46 is advantageously provided with a primary element 54 for retaining said primary anchoring arm 44, 45, 46 in the first bone 2. Respectively, each of the secondary anchoring arms 51, 52 is advantageously provided with a secondary element 55 for retaining said secondary anchoring arm 51, 52 in the second bone 3. The primary retaining element 54 is preferably formed by a row of primary retaining teeth which extend along the primary anchoring arm 44, 45, 46, and protrude from the latter in a centrifugal manner with respect to the primary free space E. Respectively, the secondary retaining element 55 is preferably formed by a row of secondary retaining teeth which extend along the secondary anchoring arm 51, 52, and protrude from the latter in a centrifugal manner with respect to the secondary free space E'.

Thus, the anchoring of the primary 4 and secondary 6 components in the bones of the patient is particularly reliable and durable, while being easy to perform.

According to a preferred variant of the primary component 5 (FIGS. 1, 2, 10 and 11), the primary anchoring body 5 preferably extends longitudinally according to the first axis A-A', and the male connector 8 extends longitudinally in a direction opposite to that of the primary anchoring body 5 according to the second axis B-B', which is preferably coincident with the first axis A-A'. Hence, the primary anchoring body 6 extends coaxially with the male connector 8, and the primary component 5 thus advantageously forms a substantially straight secondary component 5, with a substantially rectilinear average extension. Advantageously, such a primary component 4 may be combined with a substantially straight secondary component 7, that is to say with a secondary component 7 whose secondary anchoring body 8 and the female connector 9 extend longitudinally respectively according to substantially coincident third C-C' and fourth D-D' axes. Thus, a straight arthrodesis implant 1 is advantageously obtained, the primary 5 and secondary 6 anchoring bodies and the male 8 and female 9 connectors then extending longitudinally preferably according to the same direction (FIG. 1). Such an implant 1 is particularly suitable in the case where the first bone 2 and the second bone 3 should be coaxially disposed for their fusion.

According to another preferred variant of the primary component 4 (FIGS. 3, 12 and 13), the primary anchoring body 5 preferably extends longitudinally according to the first axis A-A', and the male connector 8 extends longitudinally in a direction opposite to that of the primary anchoring body 5 according to the second axis B-B', which is preferably secant to the first axis A-A'. Preferably, the second axis B-B' is then advantageously inclined with respect to the first axis A-A' at an elevation angle α comprised between 0 and 30° ($0<\alpha \leq 30°$).

Advantageously, such a primary component 4 may be linked to a straight secondary component 6, as disclosed hereinabove, thereby obtaining a bent arthrodesis implant 1. Such an implant 1 is particularly suitable in the case where the first bone 2 and the second bone 3 should be disposed according to secant average directions. Of course, the implant 1 may be designed with a different value of the elevation angle α depending on the osseous morphology and on the desired orientation between the first bone 2 and the second bone 3. Preferably, the value of the angle α corresponds to an anatomical value of the natural orientation (at rest) of the first bone 2 with respect to the second bone 3.

The invention also concerns, as such, a surgical kit (not illustrated) comprising an arthrodesis implant 1 for promoting the osseous fusion of a first bone 2 with a second bone 3, which arthrodesis implant 1 is compliant with the previous detailed description. Of course, such a kit may comprise more than one implant 1 in accordance with the invention. For example, in order to offer a wide operative choice to the surgeon, the kit may advantageously comprise a plurality of implants 1, with different sizes and configurations (straight implant 1, bent implant 1, implants with solid anchoring bodies or with anchoring arms, etc.). The kit of the invention also comprises at least:
- a first gripping instrument 56 provided with a first endpiece 57 for securing the primary component 4 of the implant 1 with the first gripping instrument 56, via the male connector 6 of the primary component 4 (FIGS. 18 to 21);
- a second gripping instrument 58 provided with a second endpiece 59 for securing the secondary component 7 of the implant 1 with the second gripping instrument 58, via the female connector 9 of the secondary component 7 (FIGS. 22 to 25).

Preferably, the first 56 and second 58 gripping instruments respectively comprise a first main body 60 and a second main body 61, for example having a rectilinear elongate general shape according to respective fifth E-E' and sixth F-F' axes of longitudinal extension, which are respectively terminated by the first 57 and second 59 securing endpieces. Preferably, the first 60 and second 61 main bodies are respectively designed to cooperate with a first and a second removable grip (or handle) (not illustrated) removably connectable to the first 60 and second 61 main bodies.

Preferably, the first 57 and second 59 endpieces are respectively designed to accommodate the male connector 6 and the female connector 9 so that the second axis of extension B-B' of the male connector 6 and, respectively the fourth axis of extension D-D' of the female connector 9, are coincident with (or at least parallel to) the respective fifth D-D' and sixth F-F' axes of extension of said first 60 and second 61 main bodies. As illustrated in FIGS. 18 to 21, the first endpiece 57 comprises an axial inner recess 62 with a shaping and configuration complementary with those of the male connector 6 of the primary component 4. This recess 62 opens axially from the first endpiece 57 via an orifice 63 with shapes and dimensions matching with the section of the male connector 6, so that the latter could be introduced (preferably completely) into the recess 62 via said orifice 63. As illustrated in FIGS. 22 to 25, the second endpiece 59 comprises, in turn, an elongate male connecting element 64, with a longitudinal average direction of extension coincident with (or at least parallel to) the sixth axis of extension F-F' of the second main body 61 of the second gripping instrument 58, and with a shaping and a configuration complementary with those of the female connector 9 of the secondary component 7. Preferably, said male 6 and female 9 connectors of the implant 1 comprising complementary locking means designed and configured to ensure a reversible relative locking of the primary 4 and secondary 7 components of the implant 1 through a quarter-turn rotation of the male connector 6 relative to the female connector 9 (as considered hereinbefore), the first securing endpiece 57 is preferably provided with a first coupling means 64 (such as for example a tooth) cooperating with the male connector 6 of the primary component 4 of the implant 1 for securing the primary component 4 with the first gripping instrument 56 through a quarter-turn rotation of the male connector 6 of the primary component 4 relative to the first securing endpiece 57, and respectively the second securing endpiece 59 is provided with a second coupling means 65 (such as for example a notch) cooperating with the female connector 9 of the secondary component 7 of the implant 1 for securing the secondary component 7 with the second gripping instrument 58 through a quarter-turn rotation of the secondary component 7 relative to the second securing endpiece 59.

As such, the first 57 and second 59 endpieces respectively may, advantageously, take on all or part of the previously disclosed characteristics of the male 6 and female 9 connectors, relating to such a reversible locking through a quarter-turn rotation. In particular, the first 64 and second 65 coupling means will preferably be designed and configured to cooperate respectively with the first locking means of the male connector 6 and with the second locking means of the female connector 9. Still preferably, said second coupling means 65 is more specifically designed and configured to enable a quarter-turn rotation of the female connector 9 relative to the second endpiece 59 only according to one direction of rotation (for example in the clockwise direction) of the female connector 9 around its fourth axis of extension D-D'. Thus, securing and then detaching the second endpiece 59 and the female connector 9 of the secondary component 7 of the implant 1 are advantageously performed through a series of quarter-turn rotations in the same direction of rotation. The rotation in the reverse direction will be in turn advantageously blocked, for example by a specific shaping of the second coupling means 65. Thus, the first 56 and second 58 instruments enable particularly easy, rapid and accurate gripping and setting of the primary 4 and secondary 7 components respectively in the first bone 2 and in the second bone 3.

Preferably, said first 56 and second 58 gripping instruments are made of a plastic material, such as polyetheretherketone PEEK, the latter being optionally charged. Advantageously, the first gripping instrument 56 and the first endpiece 57 on the one hand, and the second gripping instrument 58 and the second endpiece 59 on the other hand, form an integral part made in one piece, obtained for example by molding or machining. Alternatively, said first 57 and second 59 endpieces may constitute parts attached, whether removably or not, respectively to said first 60 and second 61 main bodies. Of course, the kit of the invention may advantageously comprise other tools or instruments possibly necessary to the implementation of at least one implant 1 in accordance with the invention, such as for example an opening instrument preferably provided with an endpiece for drilling the first 2 and second 3 bones.

Finally, an example of a surgical method for implantation, in the body of a patient, the previously-described implant 1 will be presented hereinafter. Preferably, the method includes in particular all or part of the following steps. First, an incision is performed in the body of a patient in order to reach the first bone 2 and the second bone 3. Afterwards, the joint linking the first bone 2 to the second bone 3 is sectioned in order to clear the end portions of the latter. After having, where needed, proceeded to an ablation of the cartilaginous elements present at the level of the joint, the end of the first bone 2 and second bone 3 is removed or pierced, in order to uncover their respective medullary canals. Afterwards, the interior of the medullary canals is partially or totally hollowed out in order to prepare a free hollow space for enabling the introduction of the primary 5 and secondary 7 anchoring bodies (preferably as well as the female connector 9) of the implant 1 in each of the medullary canals. Then, we proceed to an osseous resection of the dorsal area of the head or end of the second bone 3, so as to form a dorsal opening with dimensions and shape matching with the second area 18B of the opening 18 of the female connector 9.

Then, the secondary component 6 of the implant 1 is grasped using the second gripping instrument 58, preferably by locking the secondary component 6 relative to the second gripping endpiece 59 of the second instrument 58 through a quarter-turn rotation in the clockwise direction. Then, the secondary component 6 is inserted and anchored, optionally forcibly and preferably completely, into the medullary canal of the second bone 3 (FIG. 15), so that the opening 18 of the female connector 9 is positioned opposite said dorsal opening. Afterwards, the secondary component 6 is preferably detached from the second instrument 58 through a quarter-turn rotation in the clockwise direction.

The primary component 4 of the implant 1 is grasped using the first gripping instrument 56, preferably by locking the primary component 4 relative to the first gripping endpiece 57 of the first instrument 56 through a quarter-turn rotation. Then, the primary component 4 is inserted and anchored, optionally forcibly, into the medullary canal of the first bone 2 (FIG. 15), via the primary anchoring body 5, so that only the male connector 6 protrudes out of the first bone 2. Afterwards, the primary component 4 is preferably detached from the first instrument 56 through a quarter-turn rotation.

Figures 15, 16:
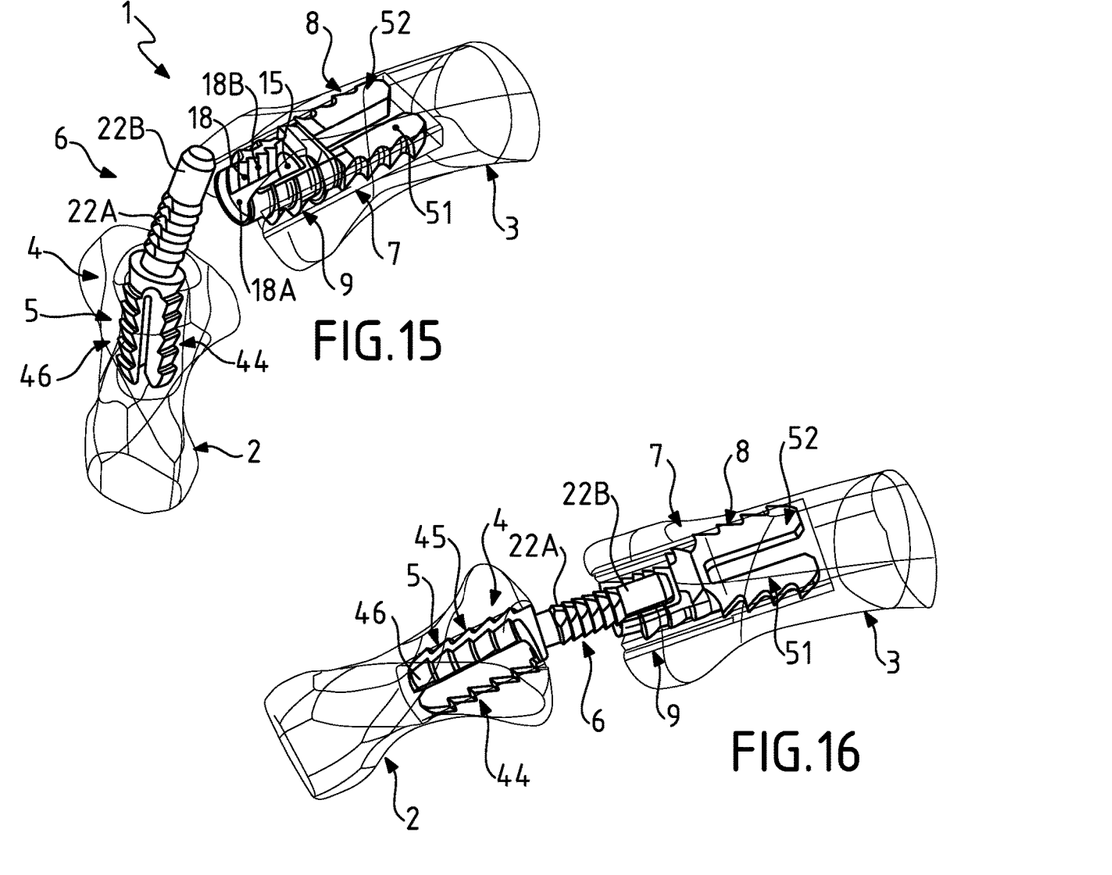
FIGS. 15 to 17 illustrate, according to perspective views, successive steps of a preferred implementation of the implant of the invention, according to the preferred second embodiment of the latter.

Afterwards, the second (end) portion 22B of the male connector 6 is laterally introduced into the housing 15 of the female connector 9, via both the first 18A and the second 18B areas of the opening 18 of the latter (FIG. 16). Then, the introduction of the male connector 6 into the housing 15 is resumed so as to bring the latter in a coaxial relative position. Afterwards, a force is exerted to bring the first 2 and second 3 bones close to each other in order to enable an axial translation (preferably according to a direction coincident with the second B-B' and fourth D-D' axes) of the male connector 6 in the housing 15 until obtaining the cooperation and the engagement of the first and second relative locking means of the primary 4 and secondary 7 components. Advantageously, this force for bringing the first 2 and second 3 bones close to each other is resumed in order to progressively adjust the relative spacing of the primary 4 and secondary 7 anchoring bodies, still preferably until joining the first 2 and second 3 bones. In this case, preferably, the primary base end 36 of the primary anchoring body 5 is then brought into contact with (or in the immediate vicinity of) the front face 12 of the main body 10 of the female connector 9. Optionally, at least one portion of the second portion 22B of said male connector 6 then protrudes from the rear end 11 of said main body 10 and extends between the secondary anchoring arms 51, 52, thereby forcing the deformation of the latter in directions opposite to each other (FIG. 17).

Possibly, this surgical method may also include a step of introducing an osteoinductive material into the respective medullary canals of the first 2 and second 3 bones, before inserting within the latter the primary 5 and secondary 7 anchoring bodies of the primary 4 and secondary 6 components. Of course, some steps of the method described hereinbefore may be advantageously omitted or performed in a different order.

The invention claimed is:

1. An interphalangeal arthrodesis implant (1) for promoting the osseous fusion of a distal phalanx (2) with a proximal phalanx (3), said implant (1) comprising:
   a primary component (4) including a primary anchoring body (5) intended to be anchored in a medullary canal of the distal phalange (2) and an elongated male connector (6); and
   a secondary component (7) including a secondary anchoring body (8) intended to be anchored in a medullary canal of the proximal phalange (3) and a female connector (9), said female connector (9) comprising:
      a main body (10) which extends longitudinally between a rear end (11) linked to said secondary anchoring body (8) and an opposite front face (12), and which has a lateral wall (14) linking said rear end (11) to said front face (12),
      a housing (15) formed within said main body (10) and configured to receive said male connector (6) in order to link together said primary (4) and secondary (7) components, and
      an opening (18) which is formed in said main body (10), in communication with said housing, (15), and which extends continuously on both said front face (12) and said lateral wall (14), and which is sized and configured to enable a lateral introduction of the male connector (6) into said housing (15) via said opening (18),
   each of said primary (4) and secondary (6) components forming an integral part made in one piece, and said primary (5) and secondary (8) anchoring bodies being respectively designed to ensure the insertion and anchoring of the primary component (4) into the distal phalanx (2), and of the secondary component (7) into the proximal phalanx (3), by impaction or by forced wedging, wherein the primary anchoring body (5) extends longitudinally between a primary penetrating end (35) for penetrating into the distal phalanx (2) and an opposite primary base end (36), and has a primary outer surface (39) linking the primary base end (36) to the primary penetrating and (35), the primary outer surface (39) having a generally convergent or conical shape, in the direction of the primary penetrating end (35), and provided with at least one longitudinal primary flattened portion (40) formed in said primary outer surface (39), wherein the secondary anchoring body (8) extends longitudinally between a secondary penetrating end (37) for penetrating into the proximal phalanx (3) and an opposite secondary base end (38), and has a secondary outer surface (41) linking the secondary base end (38) to the secondary penetrating end (37), the secondary outer surface (41) having a generally convergent or conical shape, in the direction of the secondary penetrating end (37), wherein the male connector (6) extends longitudinally between a first end (19) linked to the primary base end (36) of the primary anchoring body (5) and a second free end (20), and the male connector (6) comprises a first portion (22A) and a second portion (22B), the first portion (22A) extending from said first end (19), whereas the second portion (22B) prolongs said first portion (22A) up to said second free end (20), wherein said opening (18) of the female connector (9) comprises a first area (18A) which extends on said front face (12) and a second area (18B) which extends on said lateral wall (14) of the main body (10) of the female connector (9), said second opening area (18B) formed as a substantially rectangular window extending longitudinally from a peripheral edge (13) of the front face (12) and in the direction of the rear end (11) of said main body (10), said second opening area (18B) being shaped and configured to enable a lateral introduction of said second portion (22B) of the male connector (6) into said housing (15) via said second area (18B) of the opening (18), wherein the male connector (6) comprises a plurality of teeth (23) protruding from the first portion (22A) of the male connector (6) only, and the female connector (9) comprises a plurality of notches (24) formed along an inner wall (16) of the housing (15), the plurality of notches (24) complementary to the plurality of teeth (23) and cooperating to ensure relative locking of the primary (4) and secondary (7) components by enabling a progressive adjustment of the relative spacing of the primary (5) and secondary (8) anchoring bodies.

2. The interphalangeal arthrodesis implant (1) according to claim 1, wherein said complementary plurality of teeth (23) and plurality of notches (24) are designed and configured to ensure a reversible relative locking of the primary (4) and secondary (7) components.

3. The interphalangeal arthrodesis implant (1) according to claim 1, wherein said secondary anchoring body (8) is provided with at least one longitudinally secondary flattened portion (42) formed in said secondary outer surface (41).

4. The interphalangeal arthrodesis implant (1) according to claim 1, wherein the primary anchoring body (5) extends longitudinally according to a first axis (A-A'), the male connector (6) extending longitudinally in a direction opposite to that of said primary anchoring body (5) according to a second axis (B-B') which is coincident with said first axis (A-A').

5. The interphalangeal arthrodesis implant (1) according to claim 1, wherein the primary anchoring body (5) extends longitudinally according to a first axis (A-A'), the male connector (6) extending longitudinally in a direction opposite to that of said primary anchoring body (5) according to a second axis (B-B') which is secant to said first axis (A-A'), the second axis (B-B') being inclined with respect to said first axis (A-A') at an elevation angle (a) comprised between 0° and 30°.

* * * * *